(12) United States Patent
Song et al.

(10) Patent No.: US 9,086,326 B2
(45) Date of Patent: Jul. 21, 2015

(54) APPARATUS FOR GAS SENSING BY USING FIBER FABRY-PEROT INTERFEROMETER

(71) Applicant: Korea Institute of Science and Technology, Seoul (KR)

(72) Inventors: Yong Won Song, Daejeon (KR); Jung Ah Lim, Chungcheongnam-Do (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 130 days.

(21) Appl. No.: 13/771,642

(22) Filed: Feb. 20, 2013

(65) Prior Publication Data
US 2013/0215429 A1 Aug. 22, 2013

(30) Foreign Application Priority Data

Feb. 20, 2012 (KR) .................. 10-2012-0017070

(51) Int. Cl.
G01J 3/45 (2006.01)
G02B 6/10 (2006.01)
G01J 3/26 (2006.01)
G01J 3/02 (2006.01)
G01N 21/77 (2006.01)

(52) U.S. Cl.
CPC .......... *G01J 3/45* (2013.01); *G01J 3/0218* (2013.01); *G01J 3/26* (2013.01); *G01N 21/7703* (2013.01); *G02B 6/10* (2013.01); *G01N 2021/772* (2013.01); *G01N 2021/7723* (2013.01); *G01N 2021/7779* (2013.01)

(58) Field of Classification Search
USPC .................................. 356/450–451, 454, 460
See application file for complete search history.

(56) References Cited

FOREIGN PATENT DOCUMENTS

JP     2005-091152 A    4/2005
JP     2007-232509 A    9/2007

OTHER PUBLICATIONS

"Composite Fabry-Perot type fiber interferometer for gaseous hydrogen leakage detection", The Optical Society of Korea Annual Meeting 2009, pp. 339-340, Feb. 12-13, 2009.

*Primary Examiner* — Tri T Ton
(74) *Attorney, Agent, or Firm* — Ladas & Parry LLP

(57) ABSTRACT

The present invention relates to an apparatus for gas sensing including: a header part to generate interference wave to light from light source by the principle of fiber fabry-perot interferometer; and an optical spectrum analyzer to decide existence of specific gas based on change of spectrum periodicity of the interference wave, wherein the header part includes a sensing material that expands or shrinks by the above specific gas and the above interference wave changes its spectrum periodicity depending on expansion and shrinkage of the above sensing material.

5 Claims, 9 Drawing Sheets (a)

(b)

APPARATUS FOR GAS SENSING BY USING FIBER FABRY-PEROT INTERFEROMETER

CROSS-REFERENCE TO RELATED APPLICATION

Pursuant to 35 U.S.C, §119(a), this application claims the benefit of earlier filing date and right of priority to Korean Application No. 10-2012-0017070, filed on Feb. 20, 2012, the contents of which is incorporated by reference herein in its entirety.

BACKGROUND OF THE INVENTION

1. Field of the Invention

The present invention relates to an apparatus for gas sensing by using fiber fabry-perot interferometer.

2. Background of the Invention

With development of science and industry, discharge of harmful gas has been increasing. Accordingly, studies on gas sensor to sense harmful materials are being activated also.

Traditional gas sensors are divided into tangential firing type gas sensor and semiconductor type gas sensor, which have several problems.

The tangential firing type gas sensor is a method to sense gas concentration by converting heat of reaction between combustible gas and oxygen to electrical signals, wherein the gas burns and generates heat of combustion on the surface of catalyst, so a filter able to reduce the thermal load from this should be provided. In addition, it treats the heat of reaction to electrical signals, so is significantly affected by neighbored magnetic field or electric field.

The semiconductor type gas sensor also uses alteration of the semiconductor's electrical conductivity by making the gas absorbed by loading heat to the semiconductor, so is also affected by heat, magnetic and electric field. Besides, long time is required for loading heat to 200~300° C. and because it is sensitive to seasonal change of temperature and humidity, it may react to other gases (alcohols, solvent vapor, etc) than the gas to be sensed.

For gas sensing technology using optical manner, there are measuring devices using optical transmission and reflection and the optical manner gas sensors have merits that miniaturization and save of production cost of it is possible. Additionally, it facilitates insulation, is not interfered by electromagnetic power, and can be used for sensing pressure, humidity, chemicals, and biological molecules as remote sensing.

SUMMARY OF THE INVENTION

The present invention provides an optical apparatus for gas sensing by using fiber fabry-perot interferometer.

In addition, the present invention provides an apparatus for gas sensing that senses specific gas by using a phenomenon that according to expansion or shrinkage of polymers by absorption of specific gas, wavelength of the interference wave generated by the interferometer changes, so spectrum periodicity generated by the interference changes also.

The apparatus for gas sensing described in the present invention includes a header part to generate interference wave to light generated in the light source by the principle of fiber fabry-perot interferometer and an optical spectrum analyzer to decide existence of specific gas based on change of spectrum periodicity of the above interference wave, wherein the above header part includes a sensing material that expands or shrinks by the above specific gas and the above interference wave changes its spectrum periodicity depending on expansion and shrinkage of the above sensing material.

In addition, the above specific gas is an explosive gas including benzene series or nitro series compound.

In addition, the above sensing material is a polypyridine series polymer or a copolymer including the same.

In addition, the apparatus includes also a circulator that has the first~the third port, discharges the light generated in the light source and entering into the first port to the head part linked to the second port, and discharges the interference wave generated in the header part and entering into the second port to the optical spectrum analyzer linked to the third port.

The above header part includes an optic fiber or an optical waveguide providing a transfer route of light generated in the above light source using total reflection also and the above sensing material is coated at the end of optical fiber or optical wave guide.

Moreover, the header part of apparatus for gas sensing described in the present invention, includes an optical fiber or an optical waveguide providing transfer route of light generated in the light source using total reflection and the sensing material that is coated at the end of the above optical fiber or the optical waveguide and forms an interference wave by principle of fiber fabry-perot interferometer to the light generated in the light source and entering through the optical fiber or the optical waveguide, wherein the above sensing material expands or shrinks by the above specific gas and the spectrum periodicity of above interference wave changes depending on expansion or shrinkage of the above sensing material.

In addition, the above specific gas is an explosive gas including benzene series or nitro series compounds.

Besides, the above sensing material is a polypyridine series polymer or a copolymer including the same.

EFFECTS OF INVENTION

According to the apparatus for gas sensing described in the present invention, it is possible to provide high sensitivity in optical gas sensing based on the principle of fiber fabry-perot interferometer by using a polymer and make recovery to original state (refresh), which was a problem in conventional complex optical gas sensor, effective.

In addition, according to the apparatus for gas sensing described in the present invention, it is possible to provide superior economical efficiency, expandable property, simplicity of sensor manufacturing, and possibility of gas in/out check up in a gas sensor operating at room temperature/in the air by using the phenomenon that the spectrum periodicity changes by expansion or shrinkage of polymer caused by absorption of specific gas to the sensor.

In addition, according to the apparatus for gas sensing described in the present invention, because no additional heat source or operating power source is required to the sensor header part and it is capable of remote sensing of gas with only waveform displayed on the optical spectrum analyzer, it realizes an easy controllable and realizable optical sensor and it has a meaning as an alternative technology to the conventional nano-gas sensor with low reliability. Besides, the ultra sensitivity provided by the operating principle is suitable to sensing nitrobenzene (NB), an explosive gas, early and it is the first technical performance of the present invention to develop a polymer working to this critical gas selectively and prepare an interferometer using the same.

DETAILED DESCRIPTION OF THE INVENTION

Unless differently defined, all the terms used herein with including technical or scientific terms have the same meaning as terms generally understood by those skilled in the art relating to the field of the present invention. Terms defined in a general dictionary should be understood so as to have the same meanings as contextual meanings of the related art. Unless definitely defined in the present invention, the terms are not interpreted as ideal or excessively formal meanings. Furthermore, when the technical terms used in the present invention are unsuitable technical terms that do not precisely express the techniques of the present invention, the unsuitable technical terms should be replaced by suitable technical terms that can be understood by those skilled in the art. The general terms used in the present invention should be interpreted based on the previous or next contexts, but should not be interpreted as an excessively narrowed meaning.

A singular expression includes a plural concept unless there is a contextually distinctive difference therebetween. In the present invention, a term of "include" or "have" should not be interpreted as if it absolutely includes a plurality of components or steps of the specification. Rather, the term of "include" or "have" may not include some components or some steps, or may further include additional components.

The suffixes attached to components of the portable terminal, such as 'portion' were used for facilitation of the detailed description of the present invention. Therefore, the suffixes do not have different meanings from each other.

If it is regarded that detailed descriptions of the related art are not within the range of the present invention, the detailed descriptions will be omitted. Furthermore, it should also be understood that embodiments are not limited by any of the details of the foregoing description, but rather should be construed broadly within its spirit and scope and it is intended that the present invention cover modifications and variations of this invention provided they come within the scope of the appended claims and their equivalents.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

Figure 1:
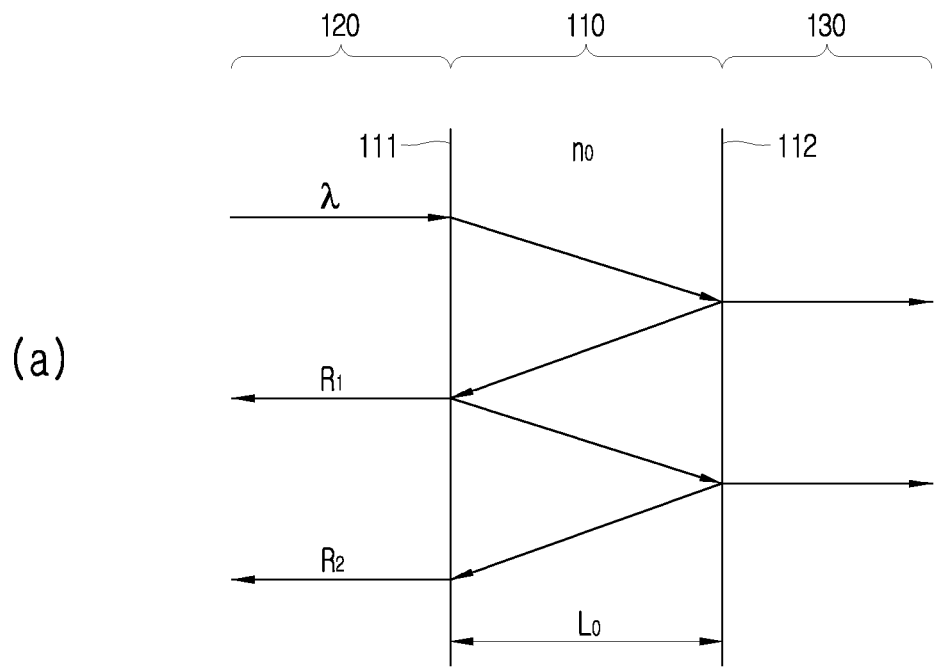
FIG. 1 is a diagram explaining the principle of fiber fabry-perot interferometer.
Figure 1:
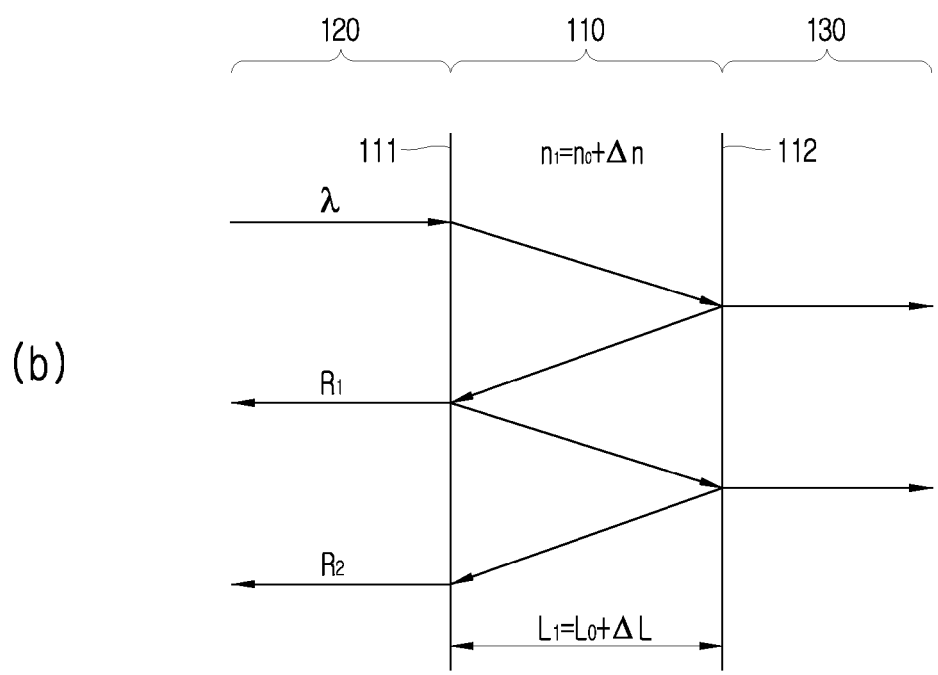

FIG. 1 is a diagram to explain the principle of fiber fabry-perot interferometer (FFPI).

The FFPI comes to have periodicity in spectrum of interference wave reflected from 2 reflectable interfaces that act as mirrors, wherein when the distance between the above mirrors or refractive index of material composing the interferometer change, the above periodicity changes also. The FFPI uses the principle to analyze spectrum using this change of periodicity. This is explained concretely below.

FIG. 1 (a) illustrates a case that the above 2 reflectable mirrors (111, 112) have a distance, $L_0$, and the space between the above mirrors is filled with a material (110) with a refractive index, $n_0$.

The above mirrors (111, 112) includes the first mirror (111), an interface to the material between the above 2 mirrors and the second mirror (112), an interface between the above material (110) and exterior.

An optical fiber (120) linked to a side of the above first mirror (111) irradiates a light with a wavelength ($\lambda$) to the first mirror (111). The light passing through the above first mirror (111) enters to the above material (130) in contact and connected with the above optical fiber (120). Wherein, when the above optical fiber (120) and the above material (130) are aligned and connected each other, the above light enters vertically with respect to the mirrors.

The light entering into the above material (110) is irradiated to the second mirror (112) and transmitted to the above exterior (130).

For the above light moving along the above route, a part is reflected and the other part is transmitted because of refractive index difference to the above optical fiber (120), the above material (110) and the above exterior (130).

Accordingly, the light which is reflected and transmitted between the above 2 mirrors (111, 112) repeatedly forms multiple reflected waves returning to the above optical fiber (120). The above multiple reflected waves (R1, R2) induces interference each other in the above optical fiber (120) and forms an interference wave finally resulted from the interference.

The above interference wave has a certain wavelength, the spectrum of the above interference wave shows periodicity according to the wavelength, and the periodicity, and the periodicity is expressed with a function by distance between the 2 mirrors (111, 112) and the refractive index of the material (110).

It is referred as FFPI to use this periodicity change of final interference wave spectrum for the purpose of sensing a material.

In this FFPI, when the above material composing the interferometer or the above refractive index of exterior change, wavelength of each reflection wave formed on the above 2 mirrors the wavelength of above final interference wave changes, so the spectrum periodicity changes also.

Finally, the FFPI can sense effects of exterior to cause material change of the FFPI by the spectrum periodicity change of the above interference wave.

FIG. 1(b) illustrates a case that the distance between 2 mirrors (111, 112) changes to $L_1$, in other words the distance between 2 mirrors (111, 112) increases by $\Delta L$.

In case that the distance between 2 mirrors (111, 112) changes, the number of final normal waves formed by reflection of the incident wave increases according to increase of resonance length, so spectrum period of the above interference wave is reduced also. Therefore, it is possible to observe a phenomenon that the shape of the spectrum crest and trough moves to one side.

If the material between the 2 mirrors (111, 112) is expanded, the material density will become lower, so not only the distance between the 2 mirrors (111, 112) will increase, but also the refractive index of the material (110) will change. Wherein, wavelength change amount according to period change of the above interference wave to wavelength of the incident wave ($\lambda$) is shown in below math equation.

$$\Delta\lambda = \frac{\lambda(n_0 \Delta L + \Delta n L_0)}{n_0 L_0}$$ [Mathematical Equation 1]

(Wherein, $\Delta\lambda$ is wavelength change of interference wave, $\lambda$ is wavelength of incident wave, $n_0$ is refractive index to the material between the 2 mirrors, $\Delta n$ is change of refractive index to the material between the 2 mirrors, $\Delta L$ is change of distance between the mirrors, and $L_0$ is the distance between the mirrors.)

The FFPI can sense effects of exterior causing change to distance of material (110) filling the space between the 2 mirrors (111, 112), based on the wavelength change of interference wave and the change of spectrum periodicity depending on change of distance between the 2 mirrors (111, 112).

Next, an apparatus for gas sensing by using the principle of FFPI is described.

Figure 2:
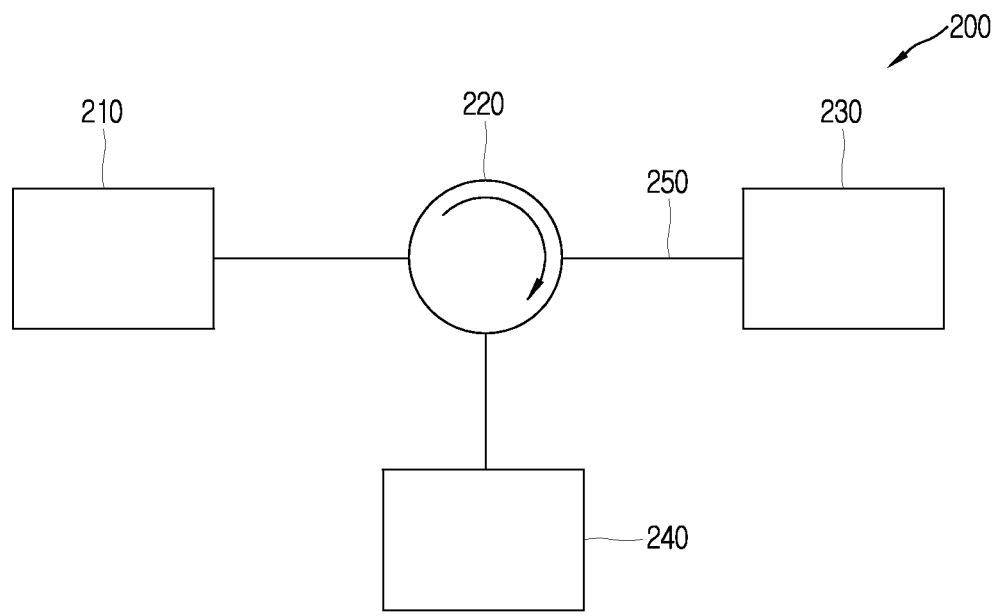
FIG. 2 is a block diagram illustrating the apparatus for gas sensing by using fiber fabry-perot interferometer described in the present invention.

FIG. 2 is a block diagram illustrating the apparatus for gas sensing by using FFPI described in the present invention.

As shown in the FIG. 2, the above apparatus for gas sensing (200) may include a light source (210), a circulator (220), a header part (230), an optical spectrum analyzer (OSA) (240), and optical fibers (250) also.

The above light source (210) can produce white or broadband light. The light produced in the above light source (210) may be irradiated into input port of the circulator (220). In addition, the above light may be irradiated into the header part (230) through the circulator (220).

The above light source (210) may be a laser diode or a broadband light source. According to an example of the present invention, the above light source (210) may be an Er-doped fiber amplifier (EDFA).

The above circulator (220) may have the first~the third port. The above circulator (220) may be configured to guide the light entering into the first port to the second port and guide the light entering into the second port to the third port.

According to another example of the present invention, the above circulator (220) can guide the light generated in the light source (210) and entering into the first port to the header part (230) connected to the second port and the interference wave generated in the header part (230) and entering to the second port to the OSA (240) connected to the third port.

Namely, the circulator (220) is located among the light source (210), the header part (230), and the OSA (240) and can convert the route of light generated is in the light source (210). Wherein, the above first port of the circulator is connected to the light source, the above second port is linked to the header part (230), and the third port is connected to the OSA (240).

The above circulator (220) may include a mirror or a polarized light control element to reflect light to control the light path.

The above header part (230) produces an interference wave by the principle of FFPI. The above header part (230) may generate the interference wave to the light irradiated by the light source (210) by the principle of FFPI.

The above header part (230) may include a sensing material working as the 2 mirror of the FFPI to generate the above interference wave. The above sensing material may make the light irradiated by the light source (210) generate the interference wave having a certain wavelength and spectrum periodicity by repeated reflect and transmission using the both ends of the sensing material as 2 mirrors.

According to another example of the present invention, the above sensing material may be expanded or shrunken by absorption with a specific gas. For instance, the above sensing material may be a material that is expanded by combination with the above specific gas and shrunken without combination with that. In addition, the wavelength of the above interference wave may change by expansion or shrinking of the above sensing material.

According to another example of the present invention, the above specific gas may be at least one explosive gas selected from the group comprising benzene series gas such as nitrobenzene (NB) and nitro series compounds such as nitromethane.

In addition, according to another example of the present invention, the above sensing material may be polypyridine series polymer or a copolymer including the same.

The concrete structure of the above header part (230) will be described in below FIG. 3 as an example in detail.

The OSA (240) decides existence of specific gas, based on the wavelength change of interference wave. Namely, the OSA (240) may decide existence of the specific gas, based on change of the spectrum periodicity by observing the spectrum of interference wave generated in the header part (230).

For this, the above OSA (240) may measure spectrum of the above interference wave. The above OSA (240) may receive the interference wave entering to the OSA (240) with a receiver (for example, photo diode etc.) and convert it to current to display its spectrum. The properties of light by the above OSA (240) may include wavelength, periodicity, and intensity of light.

Each component composing above apparatus for gas sensing (200) may be connected by the above optical fiber (250). Or the above component may be connected through planar optical waveguide instead of the above optical fiber (250).

The above optical fiber (250) may provide a path to the light generated in the above light source (210) using total reflection. The above optical fiber may connect each component composing the above apparatus for oxygen sensing (200) and provide a path to the light generated in the light source (210) to move among the components.

Concretely, the above optical fiber (250) may make the light generated in the light source (210) irradiated to the header part (230) through the circulator (220) and make the interference wave generated in the header part irradiated to the OSA (240) through the circulator (220).

The above optical fiber (250) may consist of core and cladding inducing total reflection of light to make the light move without loss of energy.

The above optical fiber (250) may be supported by ferrule. The above optical fiber (250) may be inserted to the above ferrule to compose an assembly. The above ferrule may surround lateral side of the optical fiber to support it. The above optical fiber (250) may be supported by the ferrule to maintain irradiation of light to exact position of each component.

All the components of the apparatus for gas sensing illustrated in FIG. 2 may not be essential components and an apparatus for gas sensing may be materialized by more or less components than those illustrated in FIG. 2.

Figure 3:
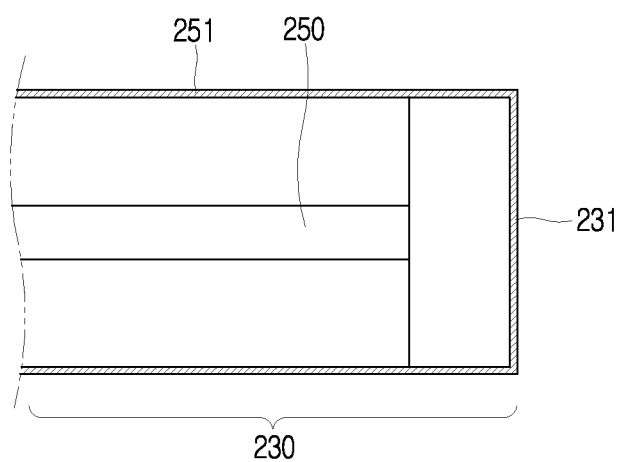
FIG. 3 is a diagram showing detailed structure of the header part in the apparatus for gas sensing according to an example of the present invention.

FIG. 3 is a diagram showing detailed structure of the header part in the apparatus for gas sensing according to an example of the present invention.

As shown in FIG. 3, the header part (230) may include an optical fiber (250) and a sensing material (231).

The above optical fiber (250) may provide a path to the light generated in the above light source (210) using total reflection. In other words, the above optical fiber (250) may provide a path to make the light generated in the light source (210) to the header part (230).

The above header part (230) may provide a path to the light generated in the above light source (210) using planar optical waveguide. The above planar optical waveguide is shorter in length and thinner in thickness than the above optical fiber (250), so it may allow intensive constitution of the header part (230) and the above apparatus for gas sensing (200) including the same (230) and be useful to change diameter of the light generated in the light source (210).

The above optical fiber (250) may consist of core and cladding inducing total reflection of light to irradiate the light to the sensor (130) without loss of energy.

The above optical fiber (250) may be supported by the ferrule (251). The above optical fiber (250) may be inserted to the above ferrule to compose an assembly. The above optical fiber (250) may be supported by the ferrule (251) to make the light irradiated to the header part (230) vertically.

The above sensing material (231) may generate an interference wave to the light irradiated by the light source (210) by the principle of FFPI.

Concretely, the above sensing material (231) may be coated at the end of optical fiber (250) (or including the ferrule (251)) and generate an interference wave to the light irradiated by the light source (210) by the principle of FFPI.

Wherein, the front end of sensing material (231) connected to the optical fiber (250) and the rear end of sensing material (231) connected to the exterior act as 2 mirrors of the FFPI and cause repeated reflection and transmission according to change of refractive index. In this process, periodical constructive interference is developed to generate multiple standing waves and as a result, final interference wave having a certain periodicity on spectrum is generated. The above interference wave generated through the FFPI by the sensing material (231) may have an arbitrary wavelength depending on the distance between the 2 mirrors and/or refractive index of the sensing material (231).

The above sensing material (231) may be expanded or shrunken by specific gas.

Concretely, the above sensing material (231) may be a material that combines with specific gas to be sensed by the apparatus for gas sensing (200) and expands. The above sensing material (231) may be expanded by combination with the specific gas and act as increasing the distance between the 2 mirrors in the principle of FFPI.

Thus, the periodicity of spectrum may be changed by expansion or shrinkage of the above sensing material (231). The above apparatus for gas sensing (200) can sense the specific gas based on the change of spectrum periodicity of interference wave.

According to another example of the present invention, the above sensing material (231) may be polypyridine series polymer or a copolymer including the same. The above polypyridine series polymer may be PnVP represented by, for example, P2VP, P4VP, and etc. In addition, the above copolymer including the polypyridine series may be PS-co-P2VP, PS-co-P4VP, and P2VP-co-P4VP.

The above sensing material (231) is a polymer easily expandable by the above specific gas and may be dissolved well in a solvent so as to facilitate preparing soft thin membrane and have good transmittance so as to be suitable for applying it as an optical sensing apparatus (sensor).

In addition, according to another example of the present invention, the above specific gas may be explosive gas. The above specific explosive gas may be at least one selected from the group comprising benzene series gas such as nitrobenzene (NB) and nitro series compounds such as nitroethane and nitromethane.

The above benzene series gas or the nitro series compounds may be classified into explosive gas and requires attention because of its large ripple effect in explosion and strong homogeneity. Especially, the above nitrobenzene is easy to be absorbed into the skin, so classified into a very dangerous material.

According to another example of the present invention, the above sensing material (231) may be coated at the end of optical fiber (250).

The method to coat the above sensing material (231) at the end of optical fiber is described below in detail.

Figure 4:
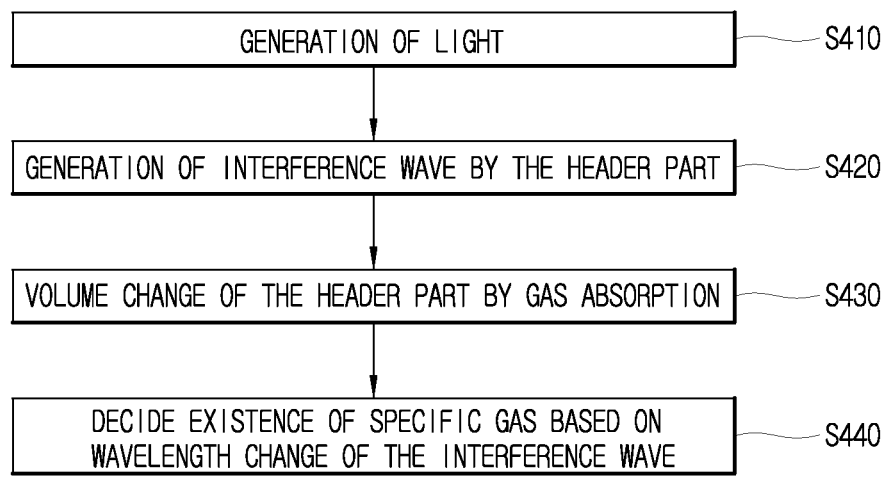
FIG. 4. is a flowchart illustrating a method for gas sensing according to an example of the present invention.

FIG. 4. Is a flowchart illustrating a method for gas sensing according to an example of the present invention.

As shown in FIG. 4, the apparatus for gas sensing (200) generate light (S410) at first.

The above apparatus for gas sensing (200) may generate light using the light source (210).

According to another example of the present invention, the above apparatus for gas sensing (200) may generate the light by using an Er-doped fiber amplifier (EDFA).

Next, the above apparatus for gas sensing (200) generates interference wave (S420).

The above apparatus for gas sensing (200) may generate interference wave to the light generated by the header part (230) by the principle of FFPI.

The above apparatus for gas sensing (200) may generate the interference wave through the sensing material (231) included in the header part (230). The above apparatus for gas sensing (200) may make the light generate interference wave with a certain wavelength by repeated reflection and transmission using both ends of the sensing material as 2 mirrors.

According to another example of the present invention, the above sensing material (231) may be changed in volume by absorption with specific gas (S430). For instance, the above sensing material (231) may be expanded by combining with the above specific gas and shrunken by disconnection of the combination with the specific gas.

For the above interference wave, its periodicity of spectrum may be changed by expansion or shrinkage of the above sensing material (231).

Finally, the above apparatus for gas sensing (200) decides existence of specific gas based on change of spectrum periodicity of the interference wave.

The above apparatus for gas sensing (200) may analyze change of spectrum periodicity by wavelength change of the interference wave using the optical spectrum analyzer (240) and decide existence of the specific gas when the spectrum periodicity is changed.

The above apparatus for gas sensing (200) may analyze if the spectrum periodicity of the interference wave is changed by combining with the specific gas and expanding of the sensing material (231). When the wavelength is changed from that when the specific gas does not exist, the above apparatus for gas sensing (200) may decide that the specific gas exists.

Next, results of sensing specific gas by using the above apparatus for gas sensing (200) according to an example of the present invention are analyzed and explained.

Below results are obtained by analyzing results for sensing nitrobenzene as the above specific gas by using polymer P4VP. As the above light source, EDFA was used and the spectrum of interference wave reflected and returning from the sensing material through the circulator by using OSA was obtained.

Figure 5:
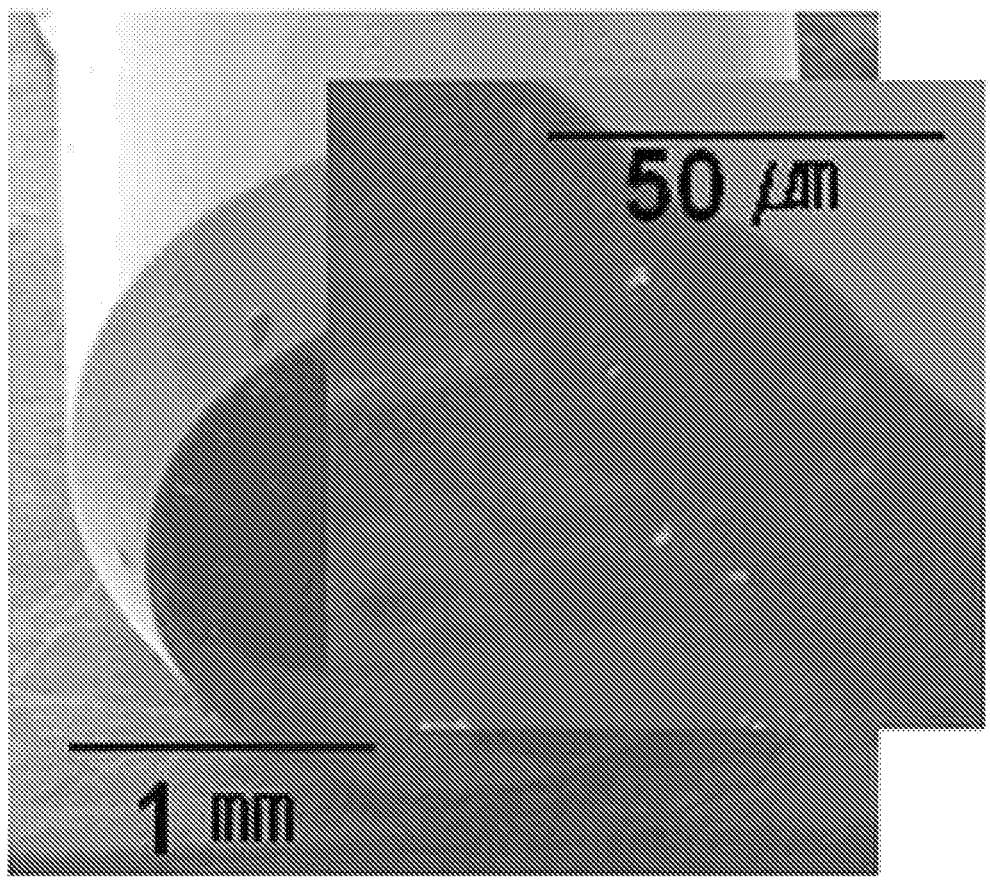
FIG. 5 is a SEM image of the header part in the apparatus for gas sensing according to an example of the present invention.

FIG. 5 is a SEM image of the header part in the apparatus for gas sensing according to an example of the present invention.

As shown in FIG. 5, an SEM (Scanning Electron Microscope) image of the header part where the polymer P4VP is coated to sense nitrobenzene is displayed.

The above SEM image was taken by using the above polymer P4VP partially coated sample in order to determine coating of the polymer P4VP.

The method to coat the above P4VP on a side of the optical fiber (250) of the header part (230) is described concretely.

First, the above P4VP may be dissolved in dimethylformamide (DMF) solvent and prepared to liquid P4VP. Wherein the ratio between the above P4VP and DMF may be adjusted.

According to an example of the present invention, the above P4VP was mixed and dissolved in the DMF solvent as 14.5 wt %.

Then, the above liquid P4VP may be coated at the end of the optical fiber (250). Wherein the above liquid P4VP may be coated by drop casting manner in order to be coated evenly at the end of the optical fiber (250).

In addition, the above liquid P4VP may be coated at the end of short patch cord instead of the above optical fiber (250) for convenience of preparation. In this case, it is possible to coat the above liquid P4VP at the end of patch cord and connect the patch cord to the end of the optical fiber (250) using a splicer.

According another example of the present invention, 0.2 µl of the above liquid P4VP was coated at the end of the patch cord.

Finally, it is possible to remove DMF solvent from the above P4VP coated optical fiber (250) through heat treatment.

According another example of the present invention, the above optical fiber received heat treatment at 80° C. oven for 30 min in order to remove effects of DMF.

Although an example of method for coating P4VP was described, the method is not limited especially in this, it is possible to coat a sensing material at the end of the optical fiber evenly and the coating method may be modified or changed if necessary.

Figure 6:
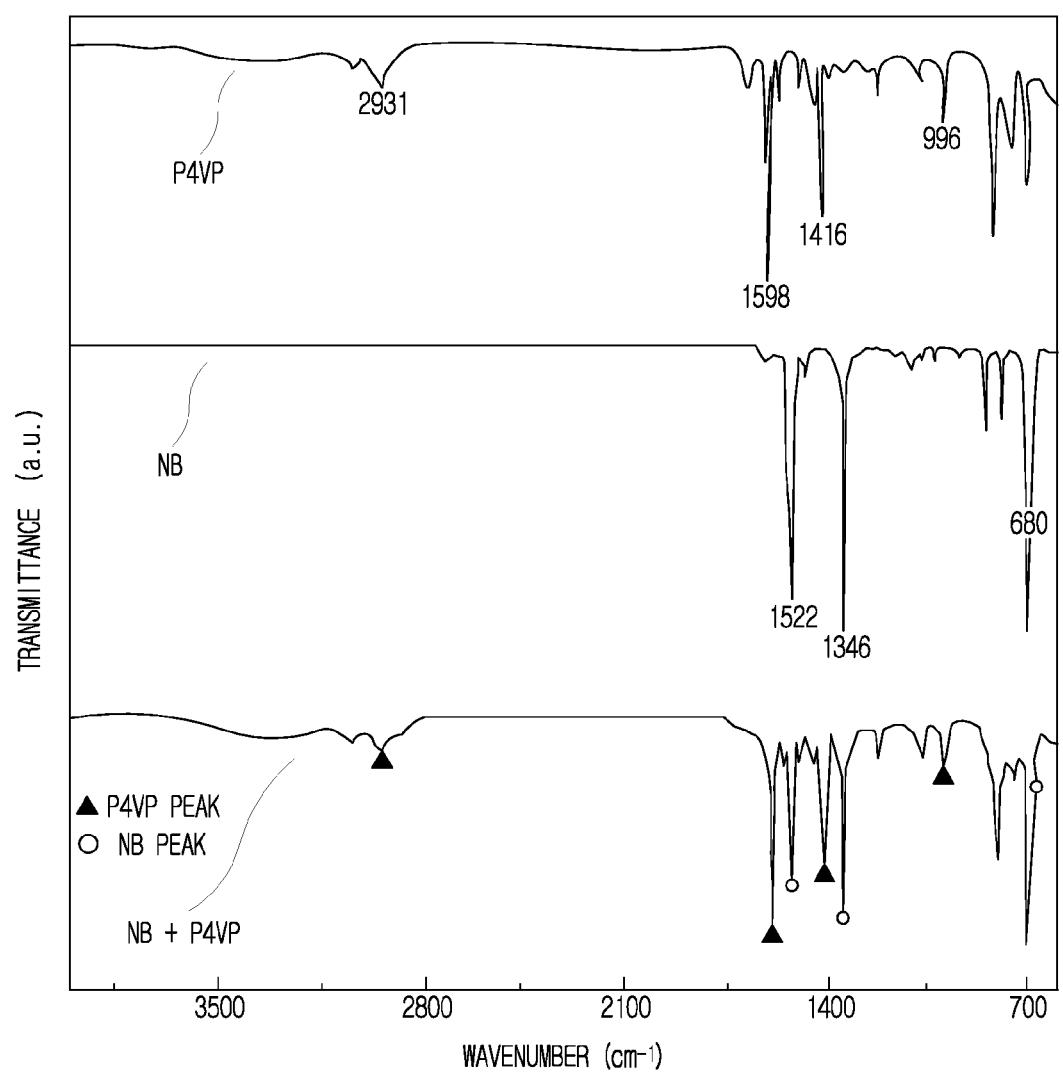
FIG. 6 is a diagram showing FT-IR curves of a pure poly (4-vinylpyridine) (P4VP) layer, an NB gas, and a NB-absorbed P4VP layer, when the P4VP was used as a sensing material in the apparatus for gas sensing according to an example of the present invention.

FIG. 6 is a diagram showing FT-IR curves of a pure poly (4-vinylpyridine) (P4VP) layer, an NB gas, and a NB-absorbed P4VP layer, when the P4VP was used as a sensing material in the apparatus for gas sensing according to an example of the present invention.

As shown in FIG. 6, it is possible to identify the absorption spectrum of the above P4VP through (Fourier transform infrared spectroscopy (FT-IR).

The absorption spectrum on the top is the absorption spectrum to the coated P4VP and the absorption spectrum on the middle is the absorption spectrum to nitrobenzene gas.

The absorption spectrum on the bottom shows an absorption spectrum in case that the coated P4VP is exposed to the nitrobenzene. Referencing the absorption spectrum on the bottom, it is found that the absorption spectrum peak appears on the P4VP absorption spectrum. This means that when the coated P4VP is exposed to nitrobenzene, and absorption of nitro benzene occurs, there's no chemical reaction between P4VP and NB gas. The physical 'mixing' of the gas into the P4VP matrix guarantees the facile refresh of the sensor.

Figure 7:
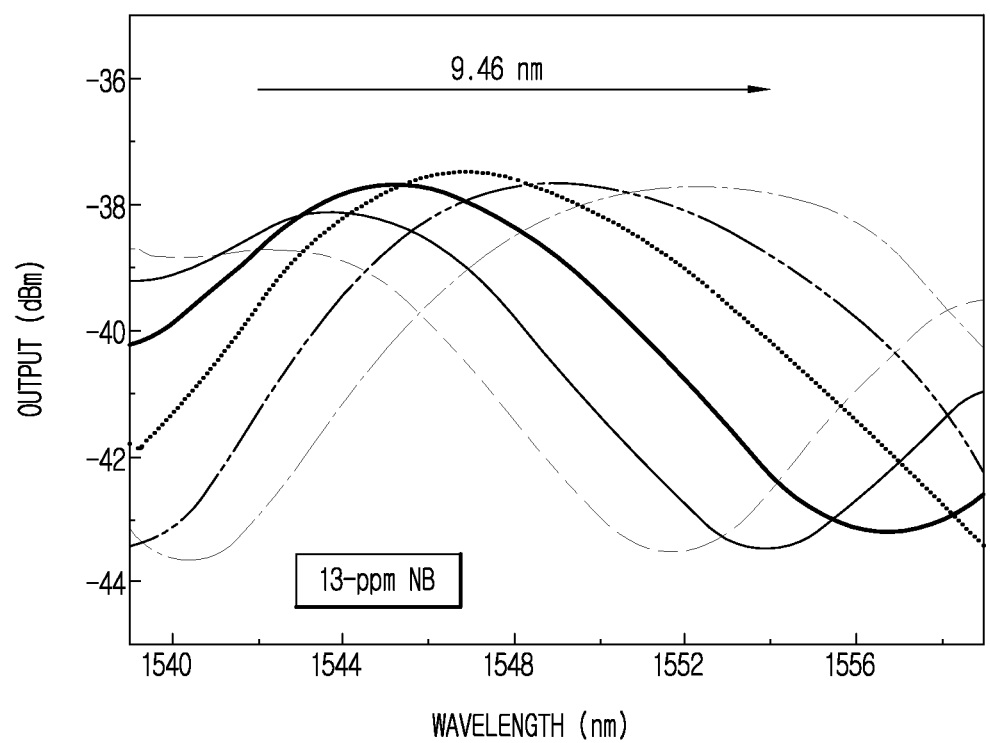
FIG. 7 is a diagram showing the results of spectrum periodicity change of the interference wave in the apparatus for gas sensing according to an example of the present invention.

FIG. 7 is a diagram showing the result of spectrum cycle change of interference wave in the apparatus for gas sensing according to an example of the present invention.

In FIG. 7, change of spectrum periodicity of the interference wave can be measured from movement of crest and trough on the spectrum, setting them.

In order to see the result of wavelength movement, a process to introduce 13-ppm nitrobenzene to the P4VP coated optical fiber was performed. Wherein, it is possible to see the changes of spectrum periodicity of the interference wave depending on time flow after introduction of nitrobenzene to the P4VP coated optical fiber on the graph.

As shown in FIG. 7, it was found that the spectrum periodicity of the interference wave started to move to long wavelength for 2.5 min. after inflow of the nitrobenzene gas In addition, it was identified that the spectrum periodicity of interference moved to short wavelength with discharge of nitrobenzene gas and then returned to the periodicity in normal state prior to the inflow of nitrobenzene.

Accordingly, it was identified that the apparatus for gas sensing that not only could sense nitrobenzene using P4VP expanded or shrunk by reaction with the nitrobenzene, but also could act as a mirror of FFPI to sense the nitrobenzene by causing spectrum change of the interference wave.

The results displayed in FIG. 7 shows that the apparatus for gas sensing of the present invention has very higher sensitivity and considerably fast reaction speed compared with conventional gas sensing apparatus.

Figure 8:
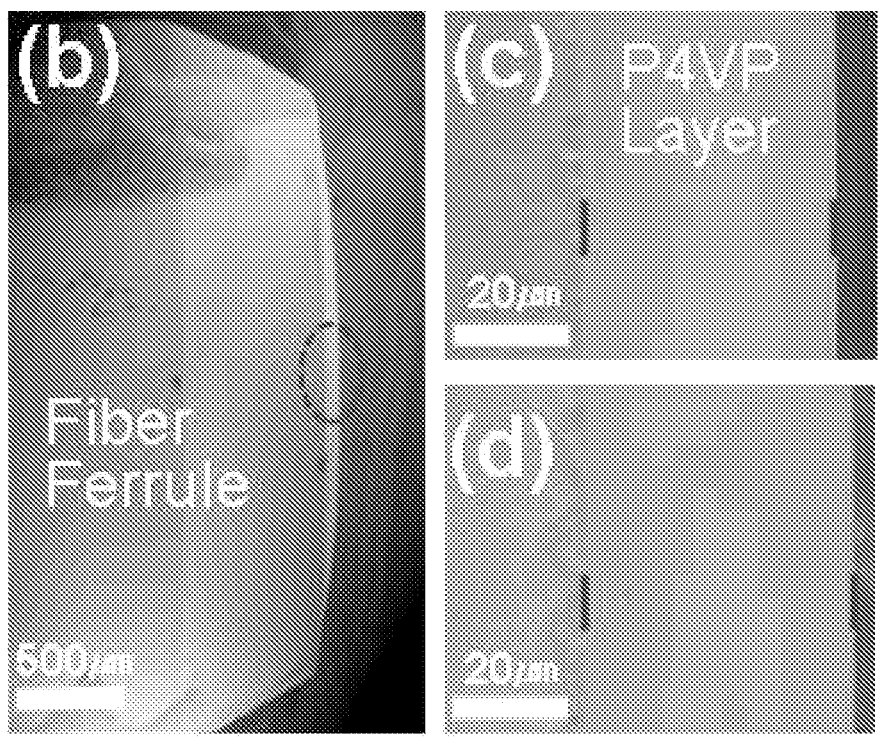
FIG. 8 is a SEM image of lateral side of the header part in the apparatus for gas sensing according to an example of the present invention.

FIG. 8 is a SEM image of lateral side of the header part in the apparatus for gas sensing according to an example of the present invention.

Referencing FIG. 8, an image obtained by SEM (Scanning Electron Microscope) on lateral side of the P4VP coated header part (230) is displayed in order to check thickness of the polymer P4VP to be expanded by inflow of nitrobenzene.

The above SEM image is illustrated dividing to before and after inflow of nitrobenzene to check expansion of the above polymer P4VP.

In addition, in order to obtain an image of the polymer P4VP changing by exposure to nitrobenzene, the SEM image was obtained at low vacuum.

Therefore, in the SEM image illustrated in the FIG. 8, expansion of the polymer P4VP was displayed, but thickness change of polymer P4VP was not displayed.

Figure 9:
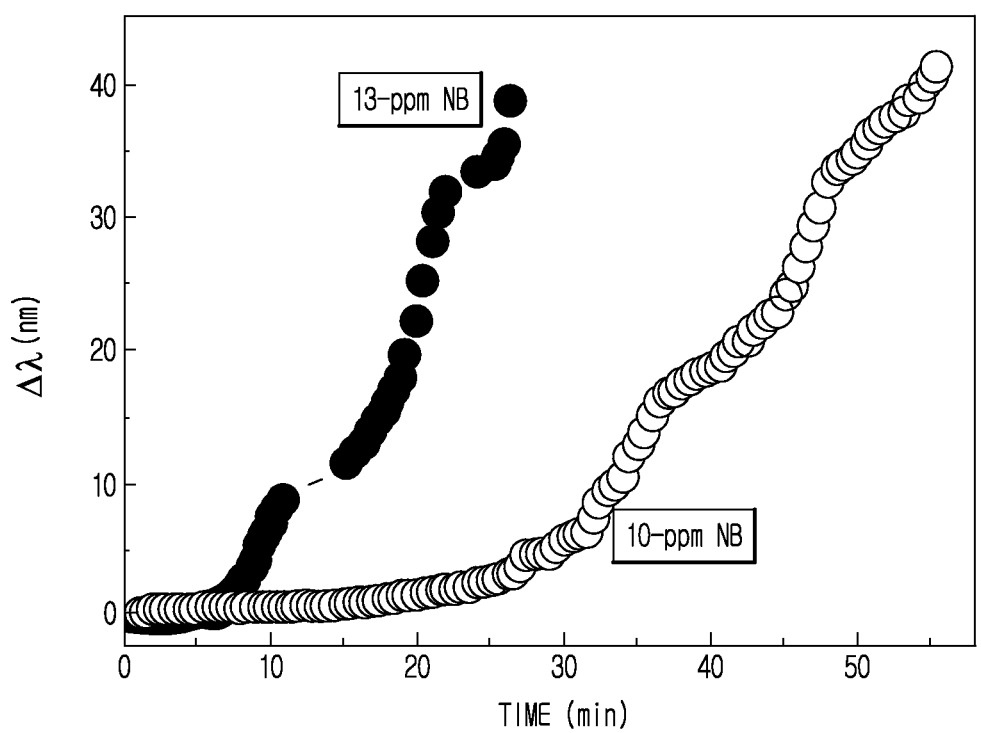
FIG. 9 is a diagram showing a test result to the header part of which sensitivity was improved through improved process.

FIG. 9 is a diagram showing test results to the header part of which sensitivity was improved through improved process.

The graph illustrated in FIG. 9 is a graph according to experimental results to identify change of spectrum periodicity of the header part of which sensitivity was improved through the improved process depending on the concentration of nitrobenzene.

Using the header part of which sensitivity was improved through the improved process, the experiment was performed at 13 ppm and 10 ppm of the nitrobenzene concentration. At this time, a separate experiment was performed by introducing at each concentration of nitrobenzene to the polymer P4VP coated optical fiber header part.

As shown in FIG. 9, it was possible to identify the change of spectrum periodicity of interference wave depending on time passage after introduction of nitrobenzene to the polymer P4VP coated optical fiber header part.

It is suggested that the periodicity change curve of interference wave depending on time passage is shown differently according to the concentration of nitrobenzene, so the periodicity of interference wave shows difference features depending on the concentration of nitrobenzene and the polymer P4VP and the nitrobenzene react each other faster and cause the periodic change at higher concentration.

Figure 10:
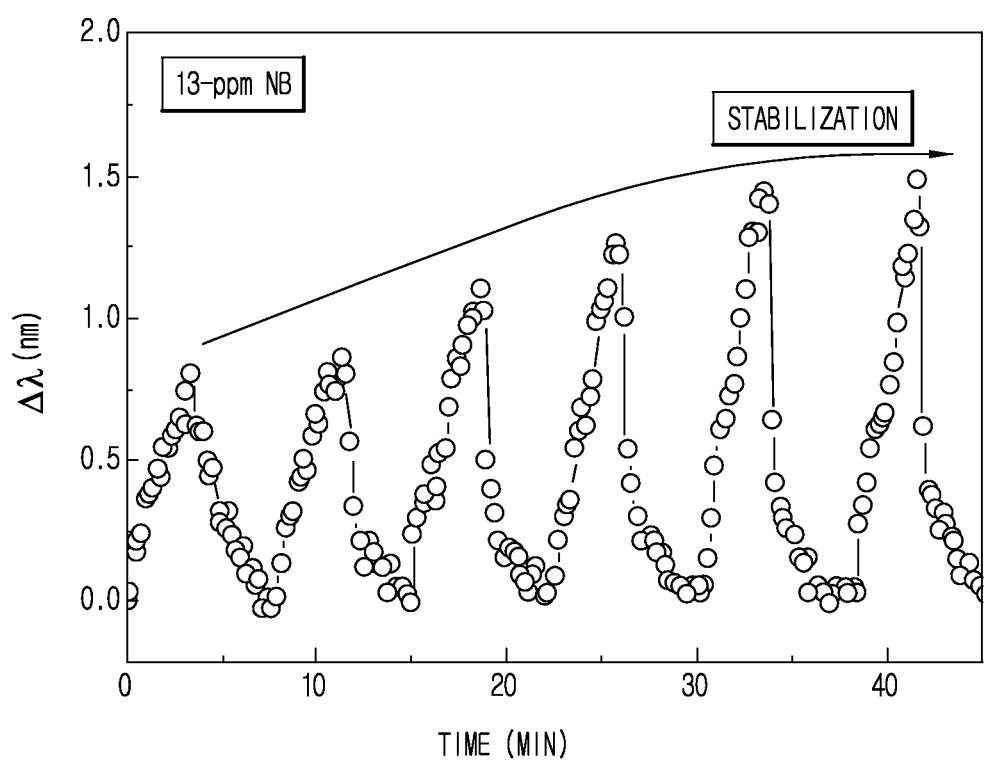
FIG. 10 is a diagram showing another test result to the header part of which sensitivity was improved through improved process.

FIG. 10 is a diagram showing another test result to the header part of which sensitivity was improved through improved process.

The graph illustrated in FIG. 10 is a graph according to experimental results to identify change of spectrum periodicity of the header part of which sensitivity was improved through the improved process to the repeated inflow and outflow of nitrobenzene.

As shown in FIG. 10, it was possible to identify periodicity change of the interference wave depending on time passage after start of inflow and outflow of the nitrobenzene to the polymer P4VP coated optical fiber.

For the spectrum periodicity of interference wave, the wavelength does not return completely to the wavelength in normal state, and it is because due to the polymer characteristics, a part of nitrobenzene molecule could not be discharged in gas outflow.

As shown in FIG. 10, it was shown that more wavelengths moved within same time in repeated inflow of the gas than its initial inflow. Therefore, it was suggested that the apparatus for gas sensing including the header part according to the present invention could have better sensitivity as well as possibility of repeated use.

As results of this experiment, it was identified that the gas sensor including the header part according to the present invention could have <5 ppb of minimum measuring range of nitrobenzene, considering that the resolution of OSA used in the sensing part was <0.02 nm.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. An apparatus for gas sensing, comprising:
   a header part to generate interference wave to light from light source by the principle of FFPI (fiber fabry-perot interferometer); and
   an OSA (optical spectrum analyzer) to decide existence of specific gas based on change of spectrum periodicity of the above interference wave, wherein the header part includes a sensing material that expands or shrinks by the above specific gas and the above interference wave changes its spectrum periodicity depending on expansion and shrinkage of the above sensing material.

2. The apparatus of claim 1, wherein the above specific gas is an explosive gas including benzene series or nitro series compound.

3. The apparatus of claim 1, wherein the above sensing material is a polypyridine series polymer or a copolymer including the same.

4. The apparatus of claim 1, wherein the apparatus includes also a circulator, that has a first, a second, and a third port, which guides the light generated in the light source and entering into the first port to the header part linked to the second port, and which guides the interference wave generated in the header part and entering into the second port to the OSA linked to the third port.

5. The apparatus claim 1, wherein the above header part includes an optical fiber or an optical waveguide providing a transfer route of the light generated in the above light source using total reflection also and the above sensing material is coated at the end of the optical fiber or the optical wave guide.

* * * * *